(12) United States Patent
Pearl et al.

(10) Patent No.: US 7,201,764 B2
(45) Date of Patent: Apr. 10, 2007

(54) APPARATUS AND METHOD FOR STIMULATING HAIR GROWTH

(75) Inventors: Henry Pearl, Boca Raton, FL (US); David Sinofsky, Boca Raton, FL (US)

(73) Assignee: Lexington Lasercomb IP AG, St. Gallen (CH)

( * ) Notice: Subject to any disclaimer, the term of this patent is extended or adjusted under 35 U.S.C. 154(b) by 0 days.

(21) Appl. No.: 10/295,487

(22) Filed: Nov. 15, 2002

(65) Prior Publication Data
US 2003/0093915 A1    May 22, 2003

Related U.S. Application Data

(63) Continuation-in-part of application No. 09/882,724, filed on Jun. 15, 2001, now Pat. No. 6,497,719.

(30) Foreign Application Priority Data
Feb. 17, 2000    (AU)   ................................. 200017548

(51) Int. Cl.
*A61N 5/01* (2006.01)
(52) U.S. Cl. ........................... 607/88; 128/898; 607/89
(58) Field of Classification Search ............ 607/88–91; 128/898
See application file for complete search history.

(56) References Cited

U.S. PATENT DOCUMENTS

| | | | | |
|---|---|---|---|---|
| 5,246,019 A | * | 9/1993 | Godfrey et al. | 132/208 |
| 5,569,368 A | * | 10/1996 | Larsky et al. | 204/600 |
| 5,616,140 A | * | 4/1997 | Prescott | 606/10 |
| 5,803,093 A | * | 9/1998 | Romano | 132/116 |

(Continued)

FOREIGN PATENT DOCUMENTS

DE    G 91 02 407.2    7/1991

(Continued)

*Primary Examiner*—Henry M Johnson, III
(74) *Attorney, Agent, or Firm*—John C. Smith

(57) ABSTRACT

A hand-held laser device that stimulates hair growth. The device provides distributed laser light to the scalp while simultaneously parting the individual's hair to ensure that the laser light contacts the individual's scalp. A unique beam splitting reflector splits a single laser beam to ensure that energy from the laser beam is evenly distributed. The reflector is mechanically aligned with the laser source and has a zigzag structure which mechanically deflects portions of the beam as it passes over the peaks of the reflector. The portions of the laser beam form a line of laser beams that project toward the individual's scalp. Parallel rows of teeth are aligned with a central row of individual laser beams and part the individual's hair to form furrows in the individual's hair as the device is combed through the individual's hair. The furrows create an unobstructed path for the laser beam to reach the scalp of the individual. Another embodiment uses a non-coherent light source to provide light energy to the individual's scalp. This embodiment also uses teeth to create a series of furrows to provide unobstructed access to the individual's scalp by the light. In this embodiment, the light source can be a series of LEDs or other lights aligned with the teeth, or a single elongated light source which provides light across the area exposed by the teeth. Another embodiment allows the use of a combination of laser light and non-coherent light.

28 Claims, 18 Drawing Sheets

U.S. PATENT DOCUMENTS 6,053,180 A * 4/2000 Kwan .................... 132/232
6,063,108 A * 5/2000 Salansky et al. ............ 607/89
6,450,941 B1 * 9/2002 Larsen .................... 600/14

FOREIGN PATENT DOCUMENTS

| JP | S62-170206 A | 7/1987 |
| JP | 2-136146 | 5/1990 |
| JP | 2-136146 A | 5/1990 |
| JP | 3-228708 | 10/1991 |
| RU | 2 114 544 C1 | 10/1998 |
| WO | WO 95/19808 * | 7/1995 |

* cited by examiner

Figure 7A
Figure 7B
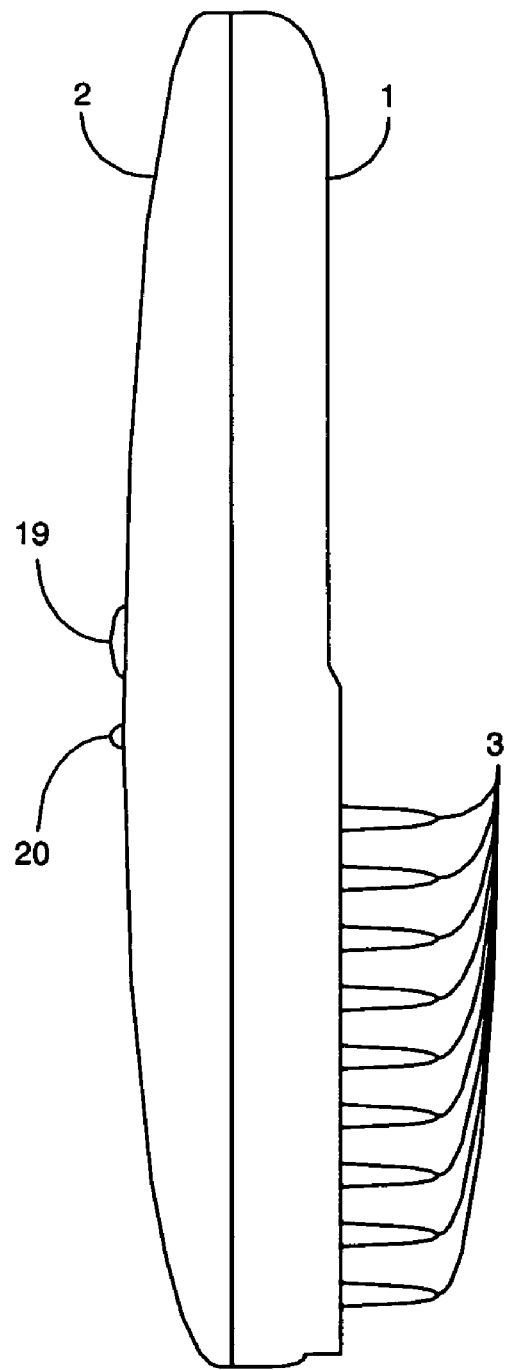
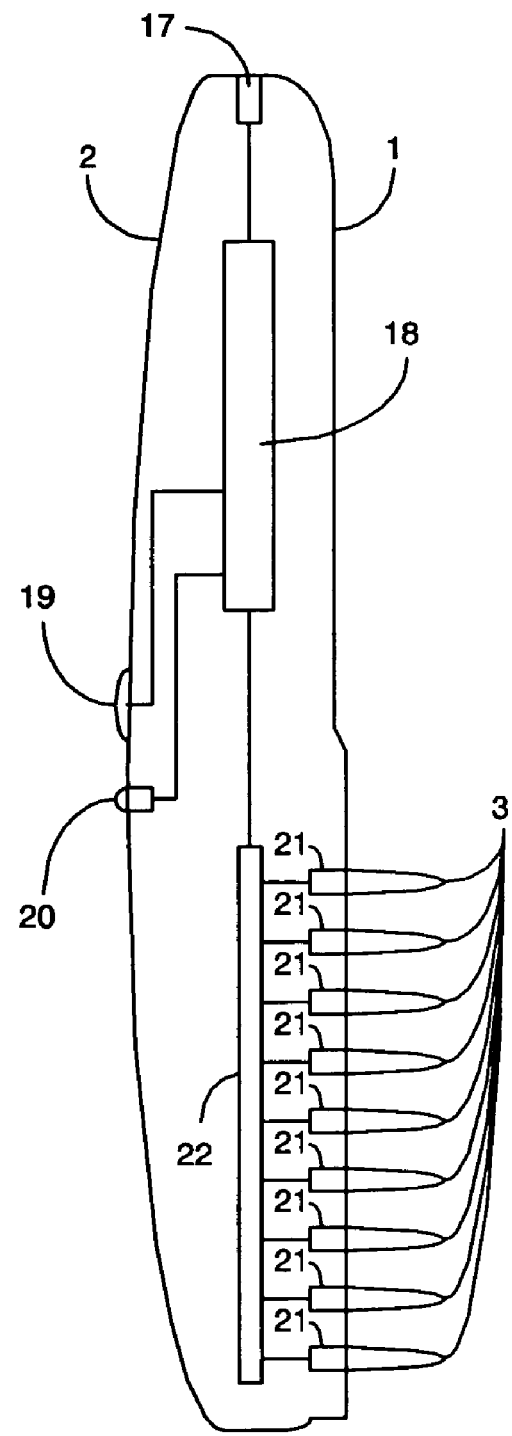

Figure 9A
Figure 9B
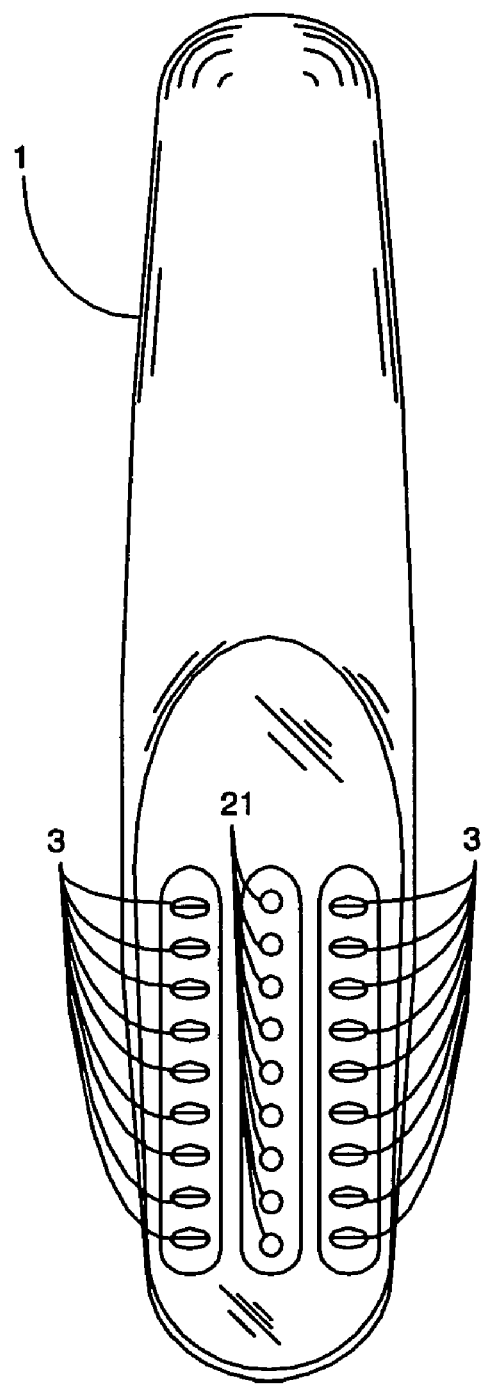
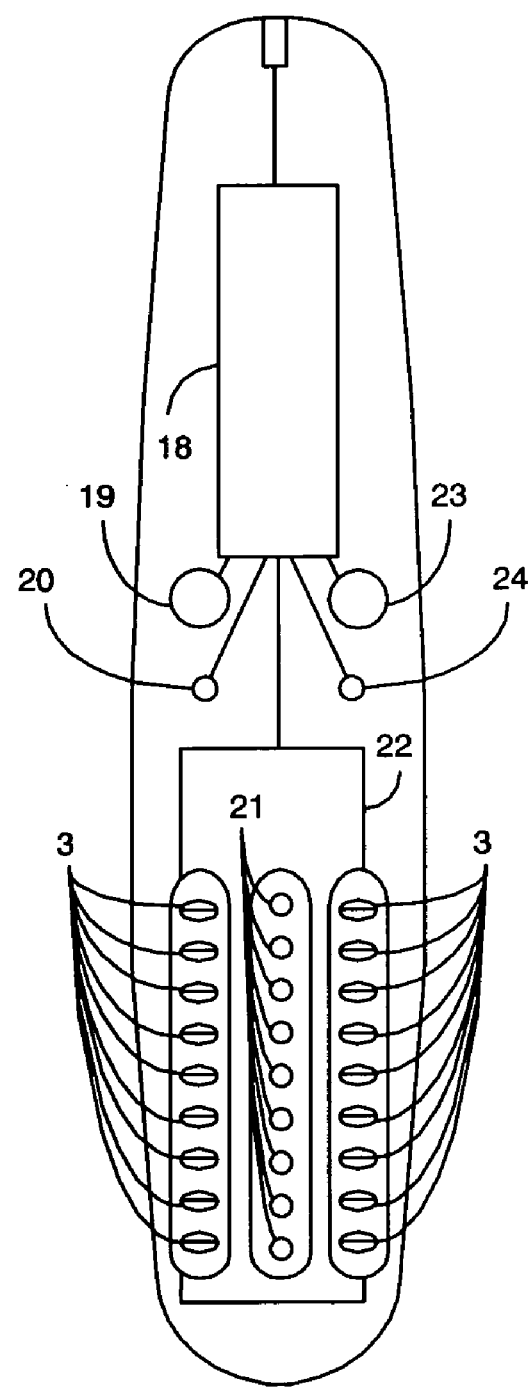

Figure 12A
Figure 12B
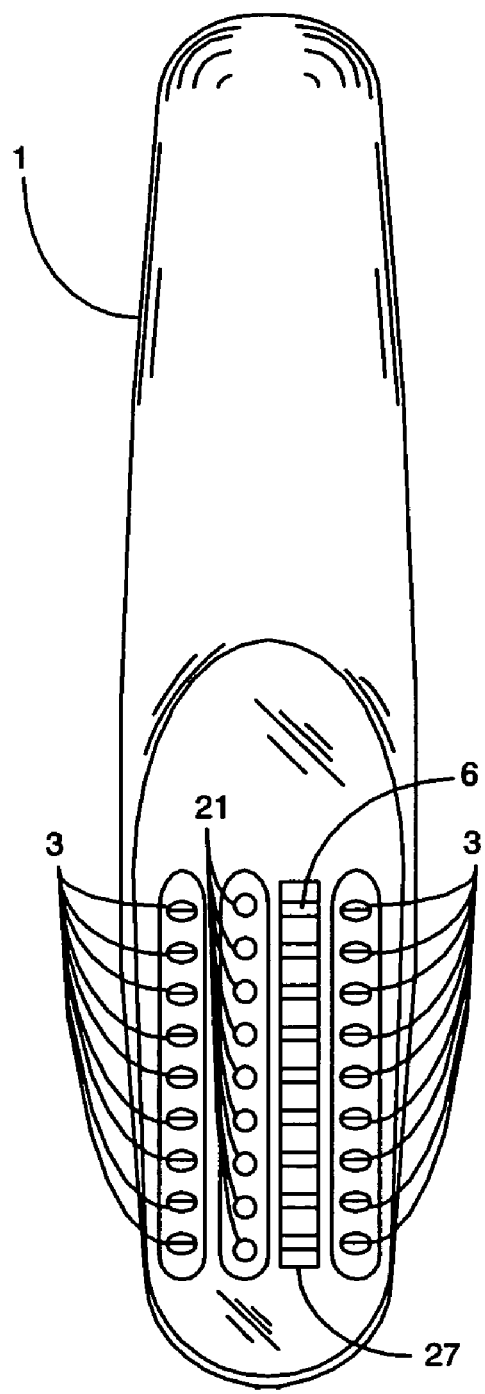
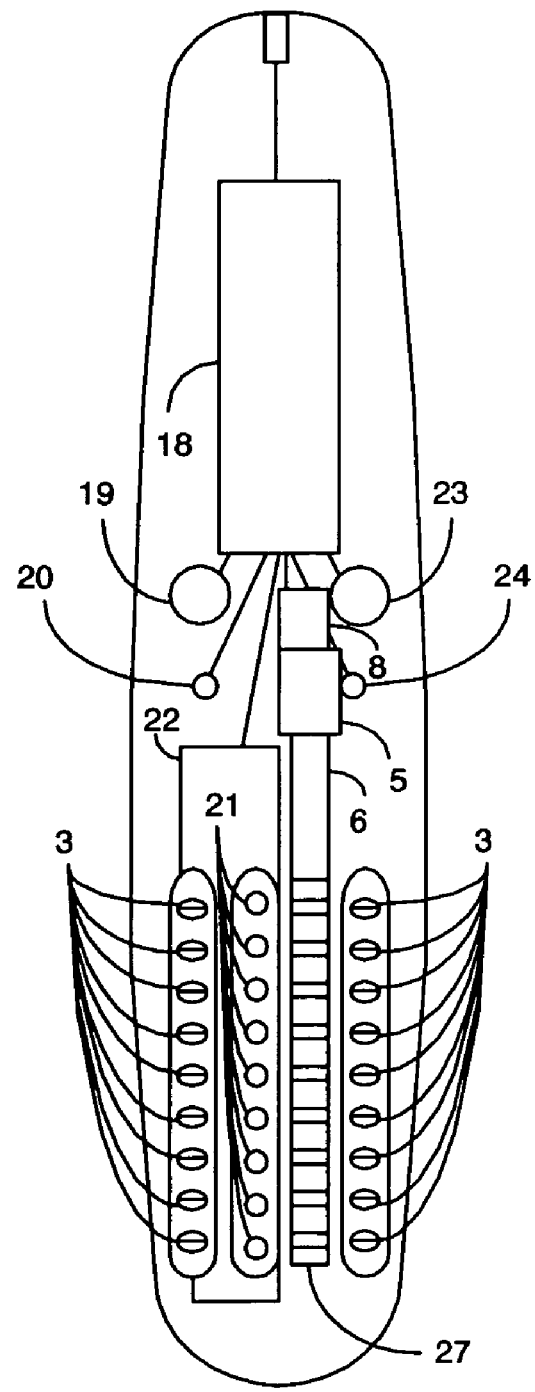

APPARATUS AND METHOD FOR STIMULATING HAIR GROWTH

CROSS-REFERENCE TO RELATED APPLICATIONS

This application is a Continuation-In-Part of the commonly owned non-provisional application entitled "Apparatus and Method for Stimulating Hair Growth," filed Jun. 15, 2001, bearing U.S. Ser. No. 09/882,724 now U.S. Pat. No. 6,497,719 and naming Henry Pearl and David Michael Sinofsky, the named inventors herein, as sole inventors, the contents of which is specifically incorporated by reference herein in its entirety which was a non-provisional continuation of the commonly owned provisional application entitled "Apparatus and Method for Stimulating Hair Growth," filed Mar. 6, 2001 and now expired, bearing U.S. Ser. No. 60/273,701 and naming Henry Pearl and David Michael Sinofsky, the named inventors herein, as sole inventors, the contents of which is specifically incorporated by reference herein in its entirety.

This application is related to, and claims the benefit of, the commonly owned copending Australian application entitled "Improved Laser comb Design/Function", filed Feb. 17. 2000, issued on Apr. 28, 2005, bearing Australian Pat. No. 200017548 B2 and naming Henry Pearl, one of the named inventors herein, as sole inventor, the contents of which is specifically incorporated by reference herein in its entirety.

BACKGROUND OF THE INVENTION

1. Technical Field

The present invention relates to a method and apparatus for treating alopecia, hair loss, and loss of hair color (i.e., greying). In particular, it relates to a method of treating the scalp or skin of an individual to increase the blood flow and general health of the skin to promote the healthier growth of hair and restoration of hair color.

2. Background Art

The loss of hair has traditionally been a problem for a substantial percentage of the population. Whether the problem is alopecia (male pattern baldness) or thinning hair, the individuals affected will generally find this to be distressing and detrimental to their appearance. In addition, the loss of hair will often make individuals appear to be older than they are. For this reason, a variety of attempts have been made to improve an individual's appearance by restoring the appearance of a full head of hair.

Early attempts to address this problem focused on the use of hair pieces (i.e., toupees or wigs). While these devices provided some degree of success, they have several drawbacks. In particular, they often have an unnatural appearance which allows them to be easily detected, even from a distance, by other individuals. In order to make one of these devices appear to be the natural hair of the wearer, they must be constructed in a fairly expensive manner using real human hair which is matched in color to the individual's remaining hair. Unfortunately, many individuals cannot afford a high quality hair piece such as this, and settle for a lower quality hair piece fabricated from synthetic fibers.

In addition, hair pieces have another drawback in that they may be inconvenient to use in situations, such as swimming, where they may become damaged or loosened. In this situation, the individual may be embarrassed due to the failure of the device. It would be desirable to improve the appearance of an individual's hair without having to resort to hair pieces fastened to an individual's head which are expensive and occasionally prone to failure due to environmental circumstances.

Those skilled in the art will recognize that more complicated mechanical solutions such as "hair weaving" exist. These more complicated solutions typically have the same drawbacks and problems as those associated with hair pieces. In addition, they are often more expensive than conventional hair pieces.

Another attempt to address this problem has been to surgically replace missing hair with "hair plugs." This surgical solution overcomes the problems created by the use of hair pieces in that the replacement hair plugs use the real hair of the individual, which results in a perfect color match and a natural appearance. In addition, the individual has no restrictions, such as those encountered in swimming and other activities, which were discussed above in regard to hair pieces. Unfortunately, this method of treating hair loss is expensive, and requires the use of medical professionals for the surgical hair transplant procedure. As a result, this procedure may not be available to a substantial portion of the public due to its high cost. It would be desirable to have a method of facilitating the growth of hair which was economically available to a substantial part of the entire public.

In addition to hair pieces and surgical transplants, pharmaceutical products have also been developed to encourage hair growth. These products can take the form of ingestible medications or topical skin treatments. Ingestible medications have been proven to encourage hair growth, but they have several significant drawbacks. In particular, they are typically prescription medications which require the cost and inconvenience of visiting a physician to obtain a prescription. In addition, the fact that they are prescription medications typically means that they will have a higher cost than non-prescription drugs. Perhaps more important than the issue of cost is the potential side effects of ingestible drugs. Quite often, the use of this type of ingestible medications may result in serious health side effects, such as damage to the individual's liver, or other internal organs, or present other serious side effects. It would be desirable to have a method of stimulating hair growth which did not carry the risks of side effects inherent in ingestible pharmaceutical medications.

Another type of pharmaceutical medication has been the use of topical skin treatments. This type of medication is often similar to prescription medications with the same cost disadvantage of ingestible medications. While some are now available as over-the-counter preparations, they typically have a reduced strength and are less effective than are their prescription counterparts. In addition, they typically have to be applied every day to achieve and maintain their desired results. It would be desirable to have an effective low-cost method of stimulating hair growth which did not require potential visits to a physician, a continuous use of expensive medications, and daily treatments to ensure results.

Scientists in Europe and Asia have found over the last 25 years that lasers can be used to stimulate hair growth. Devices have been developed having structures similar to a large floor mounted, or chair mounted, helmet. These devices contain multiple laser assemblies, and are designed to irradiate the individual's entire scalp and hair with laser energy. It is been found that there are several disadvantages associated with this approach. In particular, these are typically very large and expensive commercial devices which are found in beauty salons and spas. In order to take advantage of them, an individual will go to the establishment where the devices are located and pay for treatments on a per treatment basis. Over time, this represents a fairly expensive proposition for the individual, and typically requires a trained operator to conduct the treatment.

The helmet-like structure of this device creates an additional disadvantage. Since the device covers the head of the individual, a substantial portion of the laser energy which is intended for application to the individual's scalp is blocked by the hair of the individual, thinning though it may be, which effectively forms a canopy over the individual's scalp. It would be desirable to have an inexpensive method of applying laser treatments which does not require an individual to go to a specific location where large laser devices are used, which does not require the individual to pay every time a laser treatment is taken, and which maximizes the amount of laser energy applied to the scalp while minimizing the amount of laser energy which is blocked by the individual's hair. Likewise, it would be desirable to have a laser treatment device which has a relatively small number of lasers, and which could apply laser energy to the individual's scalp without interference by the individual's hair.

Another problem associated with hair is the loss of hair color (i.e., greying) which has the effect of making an individual appear to be older. Individuals often attempt to treat this problem by dying their hair. Unfortunately, this method of treatment has several disadvantages. For example, as was the case with hair pieces, discussed above, it can be difficult to produce the proper hair color which may make it obvious that the hair was dyed. In addition, the dyed hair tends to fade over time which results in re-appearance of the grey hair and a persistent change in color. Individuals who dye their hair typically have to re-dye their hair periodically. Of course, this represents an ongoing expense and inconvenience to the individual. Further, unless the dying process is performed by a trained individual, the results may be undesirable and unattractive. This further increases the cost of hair dying due to the need to hire a trained professional to perform the process. It would be desirable to have a method of treating loss of hair color without having to have an ongoing expense for dyes, or an ongoing expense for trained professionals to apply the dyes, and an ongoing inconvenience.

It has also been found that non-coherent light, while lacking the characteristics of power concentration inherent in laser light, can provide stimulation to the scalp which has beneficial and therapeutic effects in terms of stimulating the natural growth of hair. Unfortunately, the same problems encountered when attempting to deliver laser light to the scalp are also found when delivering non-coherent light. In particular, the problems associated with large stationary devices found in hair salons and spas, as well as the inability to penetrate an individual's hair would be found in either category of light emitting device.

While providing several methods of treating alopecia, hair loss, and greying, the prior art has failed to provide an apparatus which is inexpensive to manufacture, has a minimum number of components, minimizes the amount of laser energy blocked by an individual's hair, and can be used without leaving the individual's home or using costly commercial equipment and trained personnel.

SUMMARY OF THE INVENTION

The present invention is a hand-held light emitting device for stimulating human hair growth. The device is used by the individual and does not require trained personnel to provide a treatment. One embodiment of the device provides laser light to the scalp while simultaneously parting the user's hair to ensure that the laser light contacts the user's scalp. This embodiment users a unique, stepped, beam splitting reflector splits a single laser beam to allow an individual laser to simultaneously provide multiple laser beams which are distributed across a segment of an individual's scalp. The reflector is mechanically aligned with the laser source and has a zigzag structure which mechanically deflects portions of the beam as it passes over the peaks of the reflector. The portions of the laser beam form a line of laser beams that project toward the user's scalp. Parallel rows of teeth are aligned with a central row of individual laser beams and part the user's hair to form furrows in the user's hair as the device is combed through the user's hair. The furrows create an unobstructed path for the laser beam to reach the scalp of the user. Identical rows of teeth are placed on either side of the line of laser beams to allow the device to be combed through the user's hair in either direction.

An alternative embodiment uses a non-coherent light source to provide light energy to the user's scalp. This embodiment also uses teeth to create a series of the furrows to provide unobstructed access to the user's scalp by the light. In this embodiment, a light source can be a series of lights aligned with the teeth, or a single elongated light source which provides light across the area access by the teeth.

BRIEF DESCRIPTION OF THE DRAWINGS

FIG. 7A is a side external view of an alternative preferred embodiment which uses a non-coherent light source to provide light energy to a user's scalp.

FIG. 7B is a cutaway side view of the alternative preferred embodiment of FIG. 7A. This figure illustrates the major components used by this embodiment.

FIG. 9A is an external bottom view of the alternative preferred embodiment of FIG. 7A. This figure illustrates the alignment of multiple light sources between associated sets of teeth.

FIG. 9B is a cutaway bottom view of the alternative preferred embodiment of FIG. 7A. This figure illustrates the location of the major components used by this embodiment.

FIG. 12A is an external bottom view of the alternative preferred embodiment of FIG. 10A. This figure illustrates the alignment of multiple light sources between associated sets of teeth.

FIG. 12B is a cutaway bottom view of the alternative preferred embodiment of FIG. 10A. This figure illustrates the location of the major components used by this embodiment.

DESCRIPTION OF THE PREFERRED EMBODIMENT

Figure 1A:
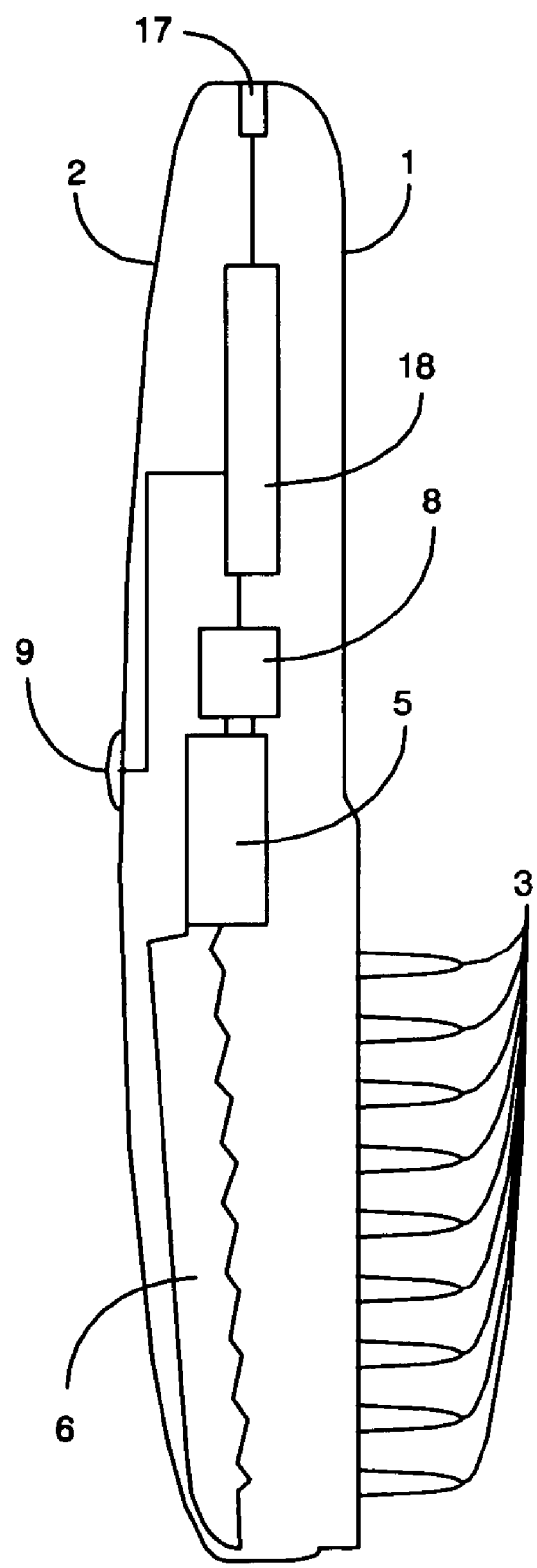
FIG. 1A is a side cutaway view of a preferred embodiment of the invention which illustrate a row of furrow forming teeth extending outward from the device, the laser beam generator, and a zigzag beam splitting reflector.

Prior to a detailed discussion of the figures, a general overview of the system will be presented. For ease of discussion, the term "scalp" will be used to describe the conventional definition which describes the hair covered portion of skin on the user's head, and in addition, any skin surface where hair is desired to be grown (e.g., a beard, etc).

It is been found that the application of light can stimulate natural processes within the body, and particularly, within the scalp such that a variety of therapeutic results can be achieved. There has been, for example, a substantial amount of research done on the use of laser energy to stimulate the bodies natural processes to heal wounds, apply skin therapy, etc. The advantage of using the coherent light of a laser is that coherent light tends to concentrate power such that a greater effect can result from the application of a particular energy level. However, non-coherent light will also produce therapeutic and healing results when applied to the skin. It only differs from coherent light in the sense that its energy is not concentrated in the form of laser beam. The device described herein has several embodiments including a laser embodiment which emits only coherent light, a non-laser embodiment which emits only non-coherent light, and a mixed embodiment which emits both coherent and non-coherent light. The general discussion of the laser, the non laser, and the next embodiments will now be presented.

It has been found that low-power lasers may be used in a variety of therapeutic applications. For example, low-power lasers are used widely for a variety of cosmetic applications such as skin care, scar reduction, wound healing and the like. In addition, it has also been found that the application of low-power laser light to an individual's scalp will assist the hair's natural ongoing replacement process and improve the scalp's condition.

One of several factors associated with the use of lasers to stimulate hair growth is that laser treatments tend to increase scalp blood circulation. In fact, studies have shown that the application of laser energy to the scalp of a user can increase scalp blood circulation by more than fifty percent without significant changes in scalp temperature. This results in the skin receiving a more abundant supply of nutrients, and in turn, the structures in the skin, such as hair follicles, also receive a more abundant supply of nutrients and necessary materials from the body.

Microscopic studies have shown laser energy increases circulation and oxygenation of the blood to the scalp and hair bulb; removes calcification and blockages around the hair bulb; as well as increases cell replacement or regenerative activity. These factors help hair to improve in fullness, shine, body and elasticity. Problems such as over-oily or dry scalp, dandruff and itchiness can also be reduced. Research on the use of cold beam lasers indicates that application of a cold beam laser to an individual's scalp will normalize metabolism of tissues, improve trophism (blood cell nutrition), and assure a regular sebaceous secretion. Measurements taken from scalps treated by cold laser indicate that hair bulbs are strengthened, hair growth can be measurably ascertained, and hair color will darken.

The increase in blood flow helps as follows: in the human scalp, the follicle in which the hair grows is attached to the scalp by a structure known as the Papilla. The Papilla provides a path for nutrients in the blood to reach the cells in the hair. The laser treatment described herein improves both the condition of the Papilla itself, as well as the blood flow reaching the Papilla. The unique structure of the handheld device presented herein provides an unobstructed path for laser light, and/or non-coherent light, to the Papilla which results in the scalp being bathed in light energy.

Another factor associated with the use of lasers is "energization." Energization can be explained as follows: Light is energy. The use of a laser light on scalp and hair follicles provides high levels of light which are used by the cells in the scalp and hair to assist in the normal chemical processes performed by those cells. The scientifically agreed-upon term for this is photobiostimulation. The most common example of light converting into chemical energy is photosynthesis, where plants are fed via light converted into chemical energy. In a similar way, laser light penetrates into soft tissue and increases the action of adenosine triphosphate (ATP), a molecule that is a major carrier of energy from one reaction site to another in all living cells. By doing so, laser light increases the energy available to cells so they take in nutrients faster and get rid of waste products. Because of this benefit, scientists and physicians have been using low level laser over the past 30 years to accelerate wound healing and regenerate tissue.

Yet another factor associated with the use of laser light is known as "vibration." Soft tissue and fluids in our bodies actually vibrate. The vibration occurs within a frequency range similar to that of cold-beam, red-light laser. In fact, one scientific theory holds that cells are largely dependant for healthy function on an exchange of energy and information with surrounding cells. This is achieved via individual wave systems by which cells communicate through inter-connective plasma by vibration. A cell is in an unhealthy state when its vibrations become irregular or out-of-step with this common communications system. However, it can be brought back into vibratory "harmony" by being irradiated with low level laser working at quantum level.

While the benefits of low-power laser treatments are known, attempts to take advantage of laser technology for the purpose of stimulating hair growth has produced limited results. In particular, when there is existing hair growth on the scalp being treated, as would be the case for individuals with thinning hair who are balding or experiencing alopecia, conventional laser beam devices do not satisfactorily penetrate the hair. As a result of the pre-existing hair blocking the path of the laser beam when it is aimed at the scalp, the effectiveness of the laser treatment is substantially reduced.

Another problem related to prior art laser treatment devices is that they tend to be large devices which are heavy and immobile. As a result, they would usually be found in a salon or clinic where the user would be charged each time the user obtained a treatment. Further, since these devices typically have fixed locations, they would not be available to the user when traveling, and they would be inconvenient to access even when the user was not traveling.

Prior art attempts to provide handheld devices have resulted in many undesirable drawbacks. For example, these devices tend to be large, bulky and complex due to the use of multiple laser modules and/or fiber optics which each produce a laser beam directed at a user's scalp. These devices also are difficult to manufacture due to the need to align the multiple lasers, or, in the case where fiber optics are used, to convey the laser energy into each fiber-optic by way of a complex lens system.

The invention provided herein solves all of the foregoing problems. The invention is a handheld, comb-like device which emits a row of laser beams which are produced by a single laser beam generator and then split into multiple laser beams by a zig-zag shaped reflector. Each laser beam in the row of laser beams has a pair of teeth which are positioned in regard to the laser beam such that as the handheld device is pulled though the individual's hair, one tooth parts the hair in front of the laser beam and the second tooth follows the laser beam holding the hair apart. By moving the hair in this manner, the two rows of teeth function to form furrows in the hair, thereby exposing the scalp of the user to the laser beam. This eliminates interference with the laser beam by the individual's hair and provides more laser energy directly to the scalp of the individual.

The invention overcomes the problem caused by pre-existing hair interfering with the laser beams by placing the laser beam generator between two rows of teeth which create "parts" (i.e., furrows) in the user's hair which are aligned with individual laser beams generated by the device. As a result of this aligned parting of the user's hair, the pre-existing hair is moved out of the way of the laser beam and the user's scalp receives the full benefit of the laser treatment.

The ability to provide multiple beams from a single laser source is provided by a unique "zig-zag" lens which splits a single laser beam generated from a single laser device into multiple parallel beams. Each beam having a power level substantially similar to adjacent beams due to their generation by a single laser source. Likewise, the use of the zigzag lens has a beam reflector eliminating alignment problems which would be inherent in systems using multiple lasers.

In one preferred embodiment of this invention, the preferred means by which the laser energy reaches the scalp is by way of a row of laser beams being preceded by a row of teeth that part the hair to expose the skin in advance of the row of laser beams. The row of teeth are aligned with the laser beams such that each tooth proceeds in advance of its respective beam to part the hair in front of the beam (i.e., forming a furrow) thereby ensuring that the beam is directed to the scalp and not blocked by the user's hair. In addition, the laser beams are followed by a second row of teeth which are also aligned with the row of laser beams. This second row of teeth allows the comb to be used in either direction for the convenience of the user. The second row of teeth also provides the benefit of keeping the hair parted for a slightly longer period of time to ensure that the hair does not fall back in place too quickly after the first row of teeth passes through the hair.

It has also been found that stimulation of the skin using non-coherent light also produces beneficial results. In particular, non-coherent light will stimulate the skin such that the ability of the skin to nourish and produce thick healthy hair is enhanced in the same manner as was done by the laser. However, the same problem encountered with delivery of laser energy to a patient's skin, namely, interference of the light beam by the patient's hair, also occurs when attempting to deliver non-coherent light energy to the skin surface. As was the case above, the comb structure used by the laser based embodiment will effectively allow access to substantial areas of the scalp by the non-coherent light.

It is also been found that a laser can be combined with a source of non-coherent light source. This provides an advantage in that while the laser uses a narrow frequency bandwidth, the non-coherent light source will deliver additional energy over a wider bandwidth. This maximizes the stimulation of the skin tissue and enhances its ability to support and nourish the growth of thick and healthy hair. In one embodiment, both laser energy and non-coherent light energy can be selectively and independently activated to provide a user with the ability to use either or both energy sources. A more detailed discussion of the figures now follows.

FIG. 1A is a side cutaway view of a preferred embodiment of the invention that illustrates the arrangement of components in the device. The components of the device are held together and supported by a lower housing 1 and an upper housing 2. Two rows of teeth 3 (only one is shown in this figure) extends down from a lower housing 1. During use, the teeth 3 are combed though the user's hair in the same manner as an ordinary comb would be used. Also shown in this figure are a laser module 8, a switch 9, a power source 18, an optional input power plug 17, a coupling assembly 5, and a laser beam splitter/reflector 6.

This unit is designed to be a self-contained, handheld, device which applies a low-level laser beam directly to the scalp of a user without having the hair of the user interfere with the laser beam. In use, the user brushes the teeth 3 through the user's hair in the same manner as the user would use a hair brush. A laser beam is aligned with each of the teeth 3 in the device such that the laser beam follows the "furrow" created by the teeth 3 as they move though the user's hair. By parting the hair in front of the laser beam in this manner, the laser beam is able to reach the bottom of the furrow (i.e., the scalp) without interference from the hair. This is a substantial improvement over prior art techniques which used helmet-like structures to direct laser energy directly to the user's head without taking into consideration the fact that most of the laser beam energy would be prevented from reaching the user's scalp by the user's hair.

Figure 1B:
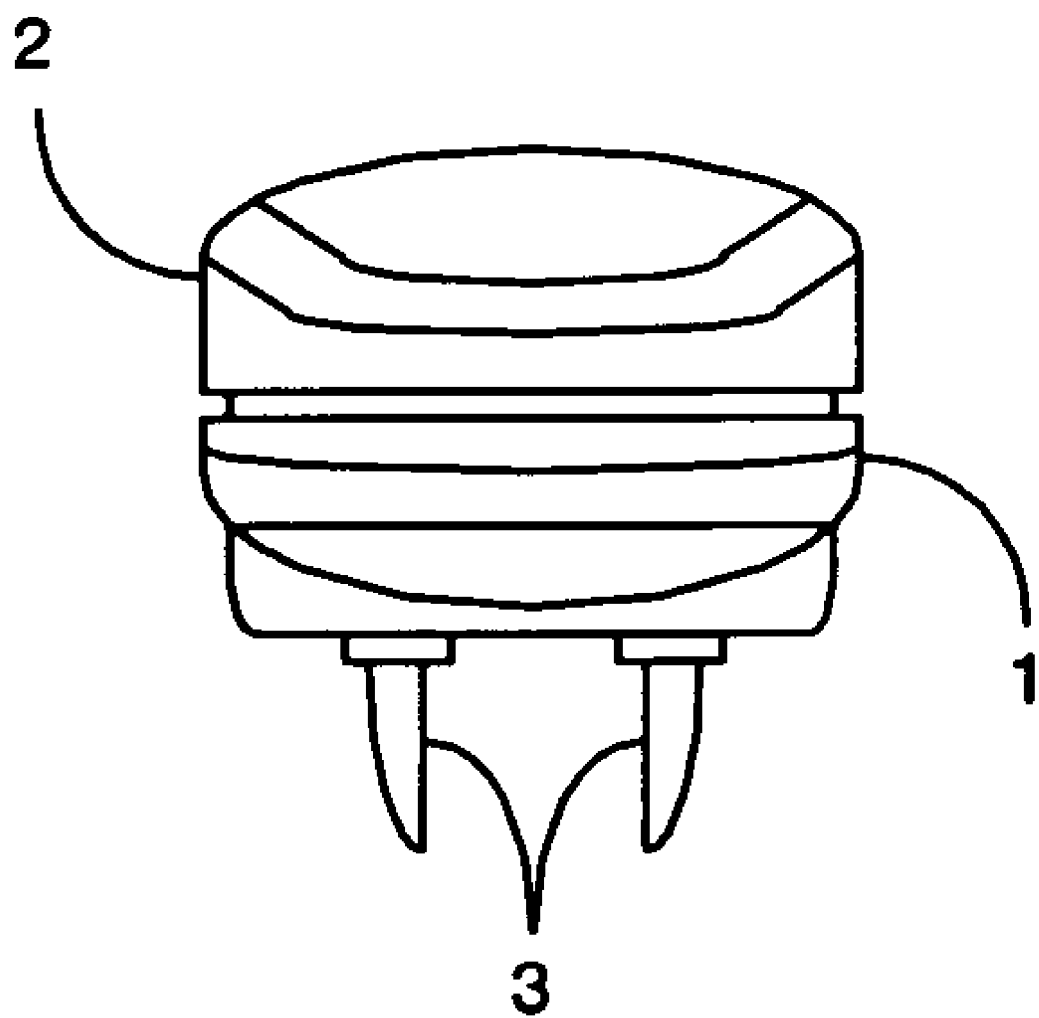
FIG. 1B is an end view of a preferred embodiment of the device which shows opposing furrow forming teeth extending outward from either side of the device.

FIG. 1B shows an end view of the device of FIG. 1A which illustrates that there are two parallel rows of teeth 3 projecting downward from the bottom housing 1. The laser beams project outward from the device between the two rows of teeth 3. Further, they are aligned with the teeth 3 such that the laser beam is projected into the furrow when the handheld device is moved in either direction across the user's scalp.

Figure 1C:
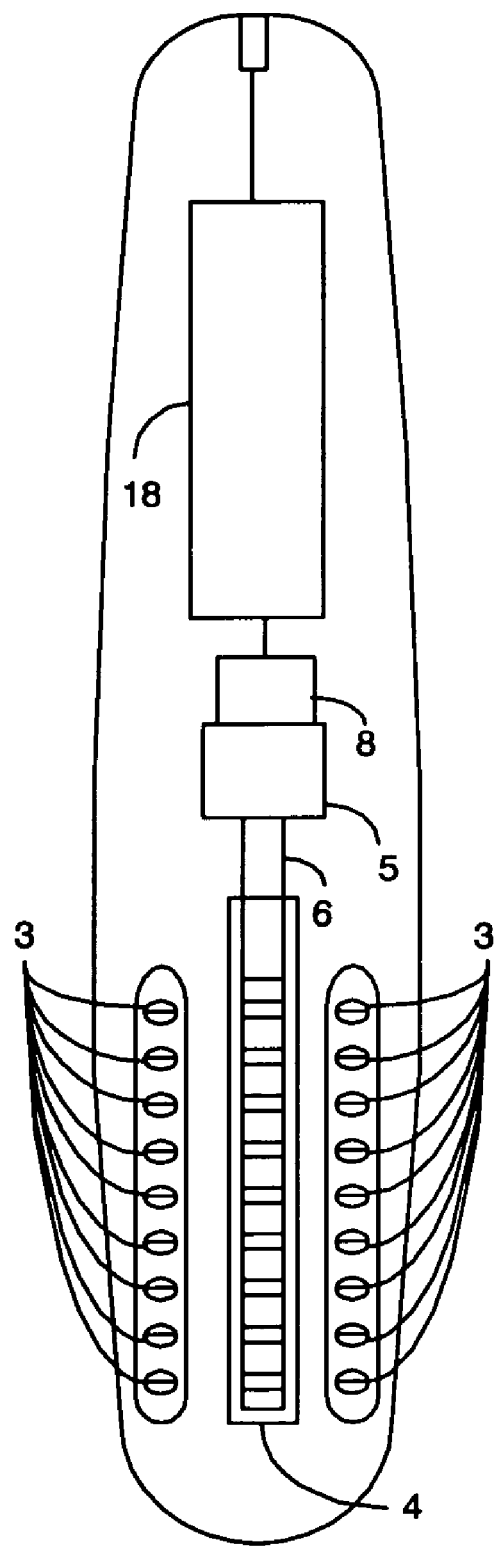
FIG. 1C is a bottom view of a preferred embodiment of the device which illustrates the two opposing rows of furrow forming teeth and the zigzag beam splitting reflector aligned with the opposing rows of furrow forming teeth.

FIG. 1C illustrates a bottom transparent view of the preferred embodiment of FIGS. 1A–B. In this view, the position and alignment of the laser reflector 6 is shown behind window 4. The laser reflector 6 is placed between the two rows of teeth 3 such that, whether the handheld device is moved forward or backward across the scalp, there is always a tooth 3 available in front of each laser beam to ensure that a furrow is created for each laser beam to reach the scalp. This results in a more effective application of laser energy to the scalp than was heretofore possible in prior art devices.

In addition to being more effective than prior art devices in terms of the actual application of laser energy to the scalp, the embodiments disclosed herein are also superior to prior art devices in that they are extremely lightweight and portable. They can be manufactured such that they can be plugged into a wall socket for electrical energy, or alternatively, it can be battery operated to further add to the user's convenience. In addition, the reflector 6 allows a single laser to be used rather than the multiple lasers used by prior art devices.

Figure 2A:
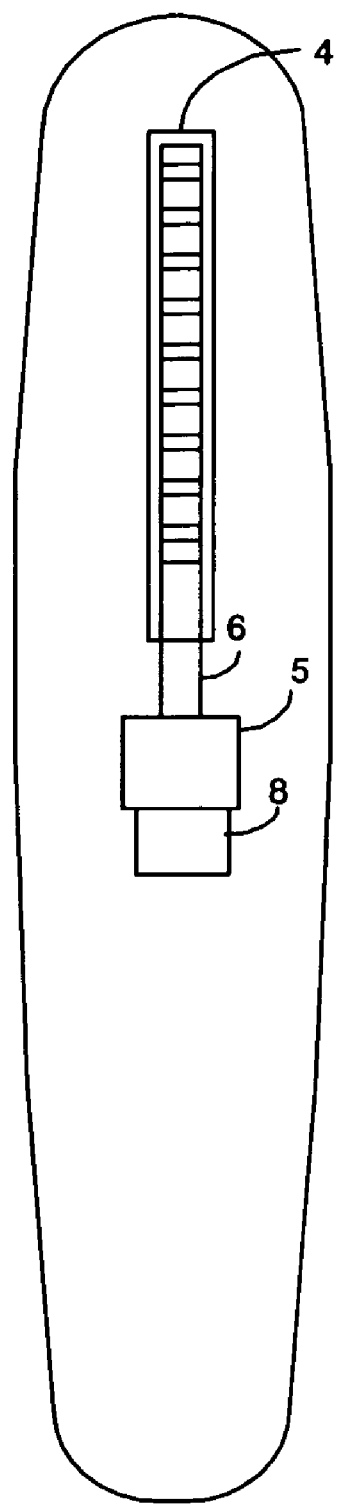
FIG. 2A is a bottom view of a preferred embodiment of the device which illustrates the zigzag beam splitting reflector attached to the laser beam generator.

In FIG. 2A, a bottom transparent view of a preferred embodiment of the handheld device is illustrated. For ease of discussion, several items have been eliminated from this figure which is intended to show the relative position of the reflector 6 in relation to a window 4. The window 4 provides a transparent cover for the reflector 6. This allows the reflector 6 to be sealed within the handheld device to protect it from contamination such as dust, water vapor, water, etc.

Figure 2B:
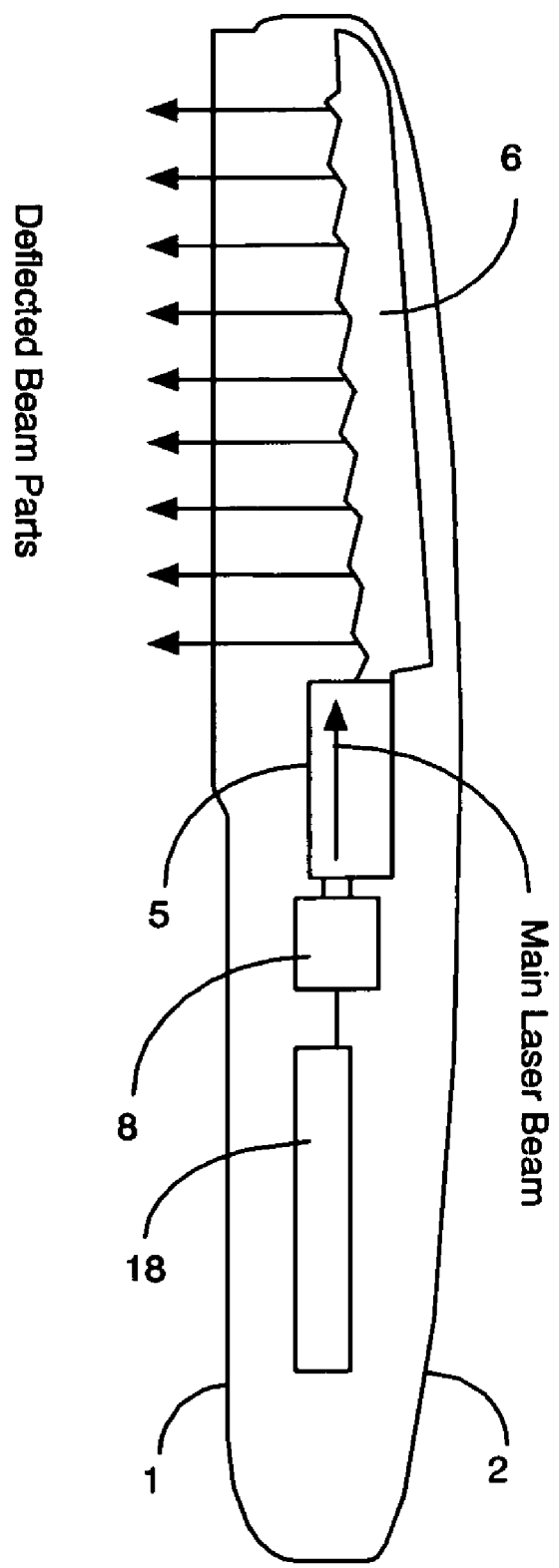
FIG. 2B is a side cutaway view of a preferred embodiment of the device in which the single laser beam is shown being split into several portions which are deflected as a parallel line of laser beams

FIG. 2B is a cutaway side view of a preferred embodiment of the invention which shows the path of the laser beam across the zigzag edge of the reflector 6. As the laser beam strikes the various steps of the zigzag edge of the reflector 6, portions of the laser beam are distributed as several reflected beam parts which are reflected downward and out through the window 4 toward the furrows formed in the user's hair by the teeth 3. The zigzag reflector 6 provides a substantial advantage to the user in that, since a single laser beam is used, each reflected beam part will have substantially the same amount of energy. This avoids the situation which could happen if multiple lasers were used to generate individual beams, because a multiple laser system could result in hot spots created by any substantial discrepancies in the output power produced by individual lasers.

Figure 3:
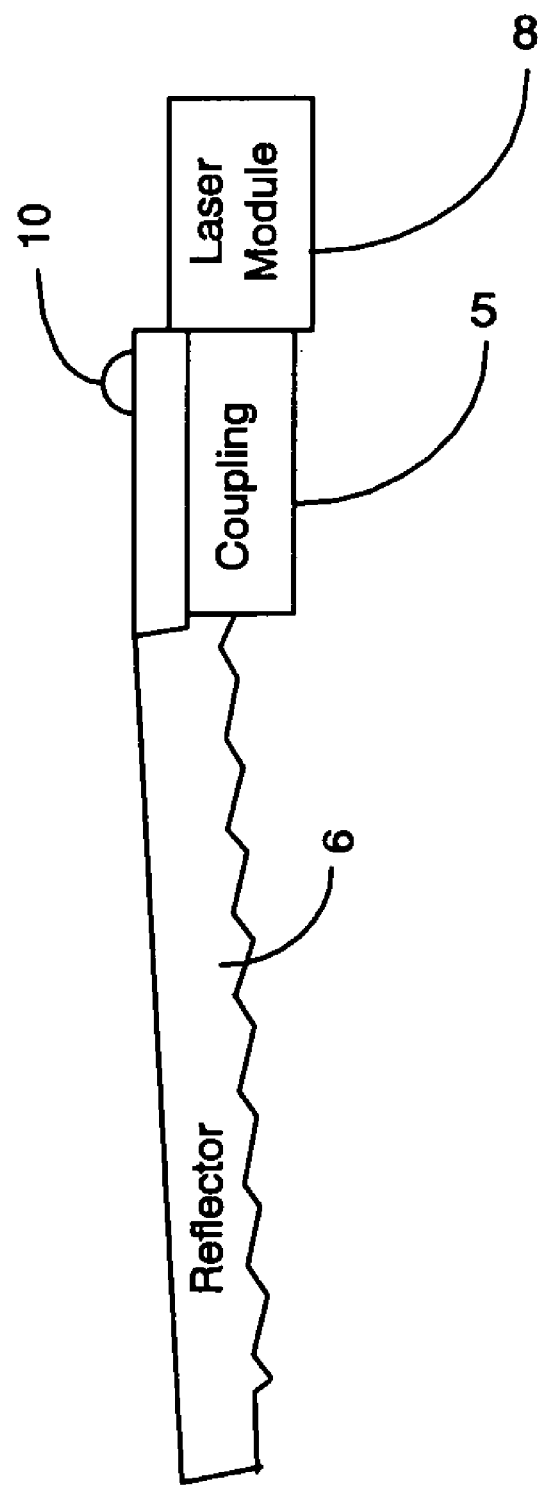
FIG. 3 is a side view of a preferred embodiment of the laser assembling which includes the laser module and the zig-zag beam splitting reflector

FIG. 3 illustrates the use of a coupling device 5 to align the laser 8 with the reflector 6. This type of mechanical alignment system substantially enhances the ease of manufacture and allows parts to be interchangeable. Further, it eliminates the substantial alignment problems which would occur in a multiple laser system that require each laser to be individually adjusted during manufacture.

Figure 4A:
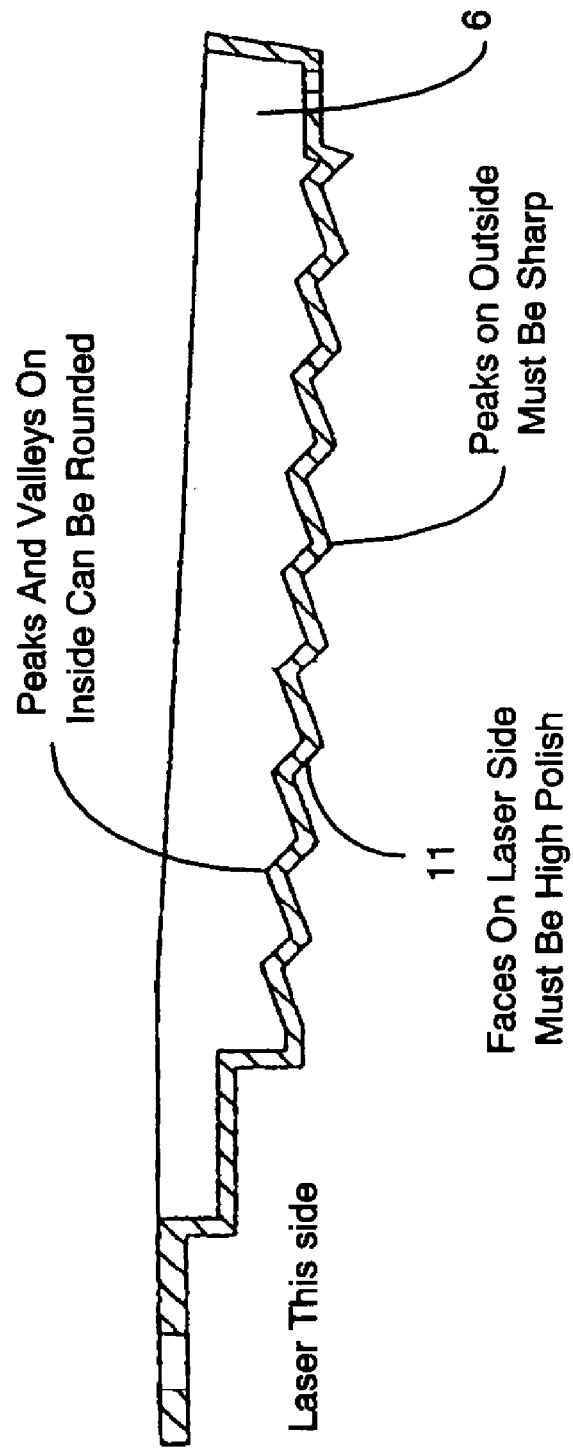
FIG. 4A is a side perspective view of a preferred embodiment of the zigzag beam splitting reflector.

FIG. 4A provides more detail concerning the structure of the reflector 6 which is used in the preferred embodiment. To ensure that the maximum amount of energy is deflected in the proper manner, the face 11 on the reflector 6 which is stuck by the laser must have a high polish and reflectivity. While the peaks and valleys on the inside of the reflector 6 can be rounded, the peaks and valleys on the outside of the reflector 6 must be sharp to avoid defusing the laser beams.

Figure 4B:
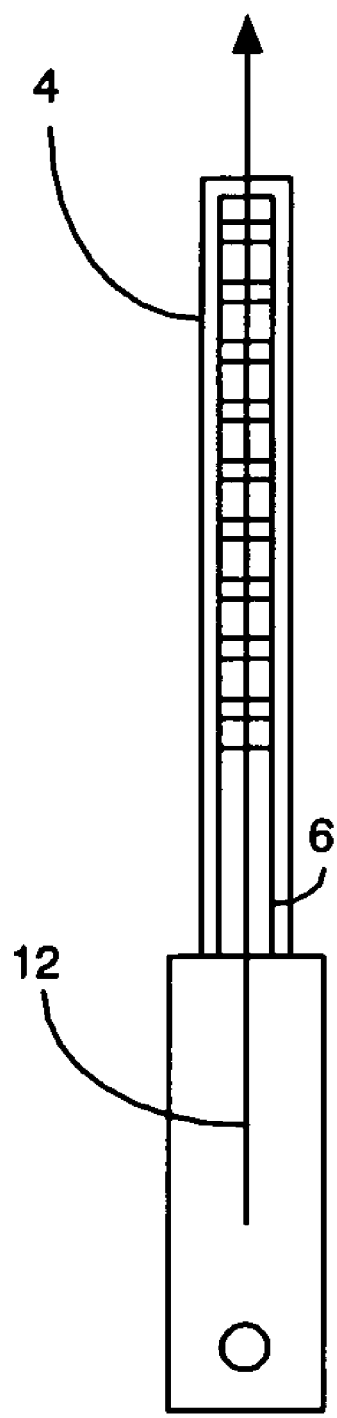
FIG. 4B is a bottom view of a preferred embodiment of the zigzag beam splitting reflector.

In FIG. 4B, a bottom view of the reflector 6 is shown which illustrates the path of the laser beam when it is projected from the laser. The laser beam is directed across the central portion of the reflector 6 to ensure that laser energy is not wasted by projecting some of it past the edge of the reflector 6.

Figure 4C:
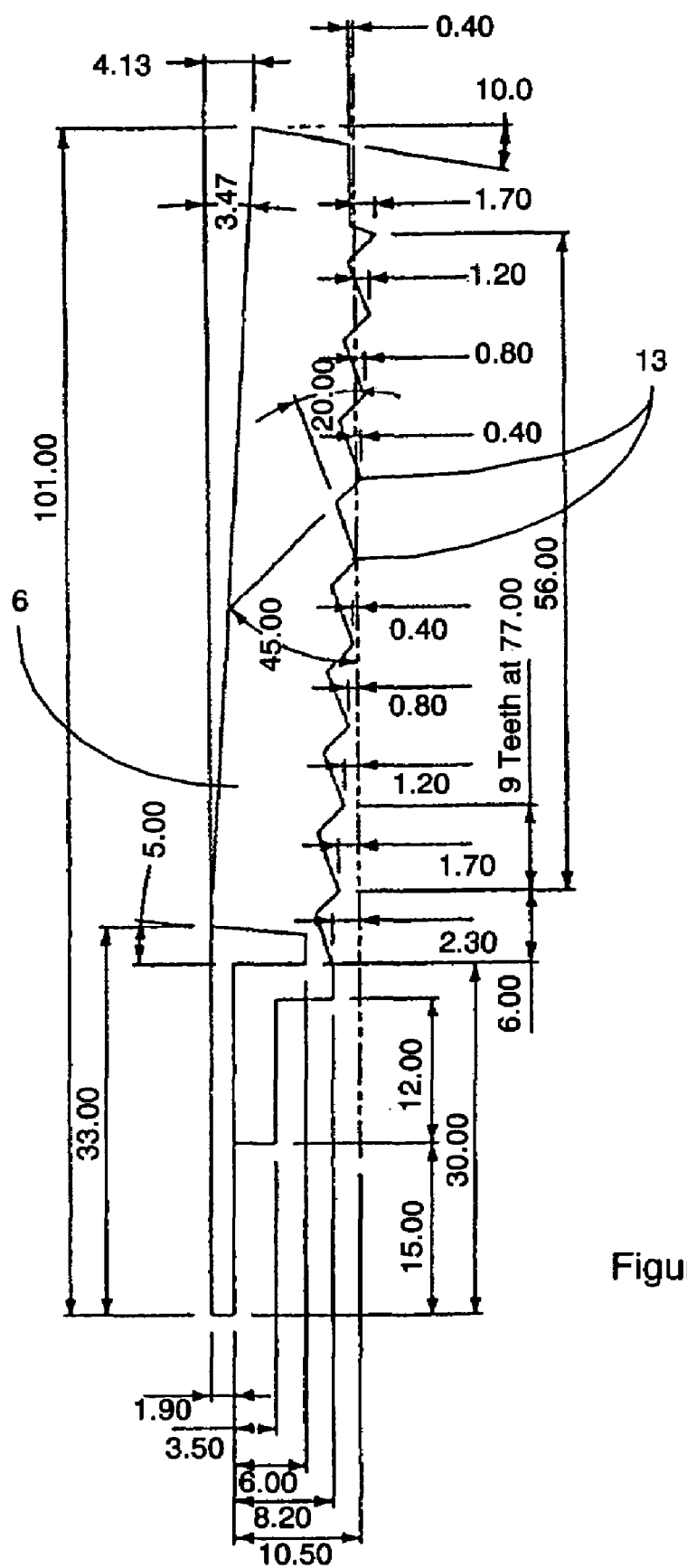
FIG. 4C is an illustration of a preferred embodiment of the arrangement of teeth on the zigzag beam splitting reflector.

FIG. 4C provides more detailed information regarding the structure of the reflector 6. As can be seen in this figure, the zigzag structure of the reflector 6 places steps 13 which are more distant from the laser source at progressively lower elevations such that as the laser beam is projected outward from the laser's lateral path, each step 13 intercepts and deflects a portion of the laser beam. By aligning specific amounts of area to each deflected beam, a uniform distribution of power can be achieved by splitting the single laser beam.

Figure 5A:
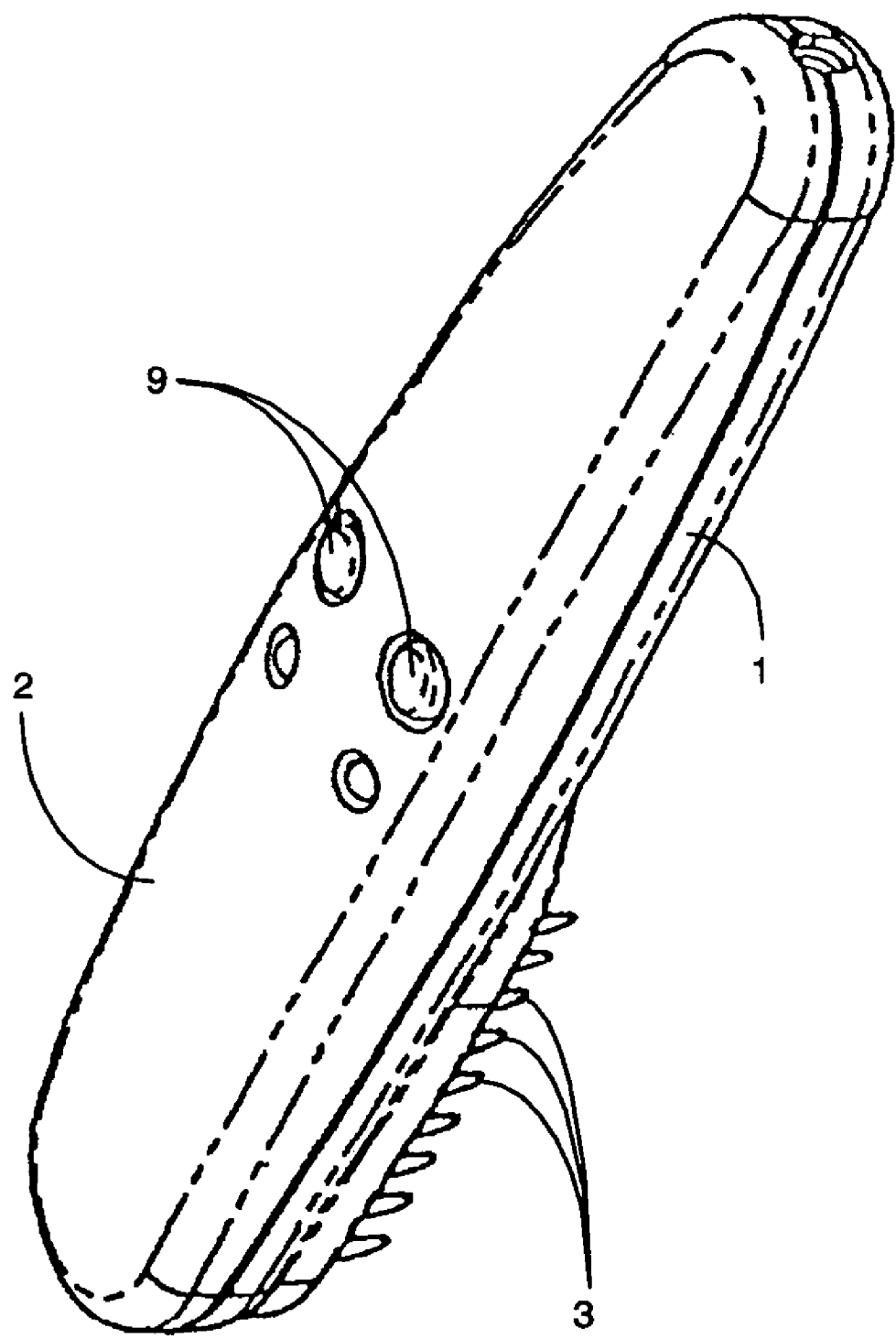
FIG. 5A is a top perspective view of a preferred embodiment of the device which illustrates the control switches on the top of the device and the furrow forming teeth extending from the bottom of the device.

FIG. 5A is a perspective view of a preferred embodiment of the handheld device. In this view, the teeth 3 are shown projecting downward from lower housing 1, and control switches 9 are shown located on the upper housing 2.

Figure 5B:
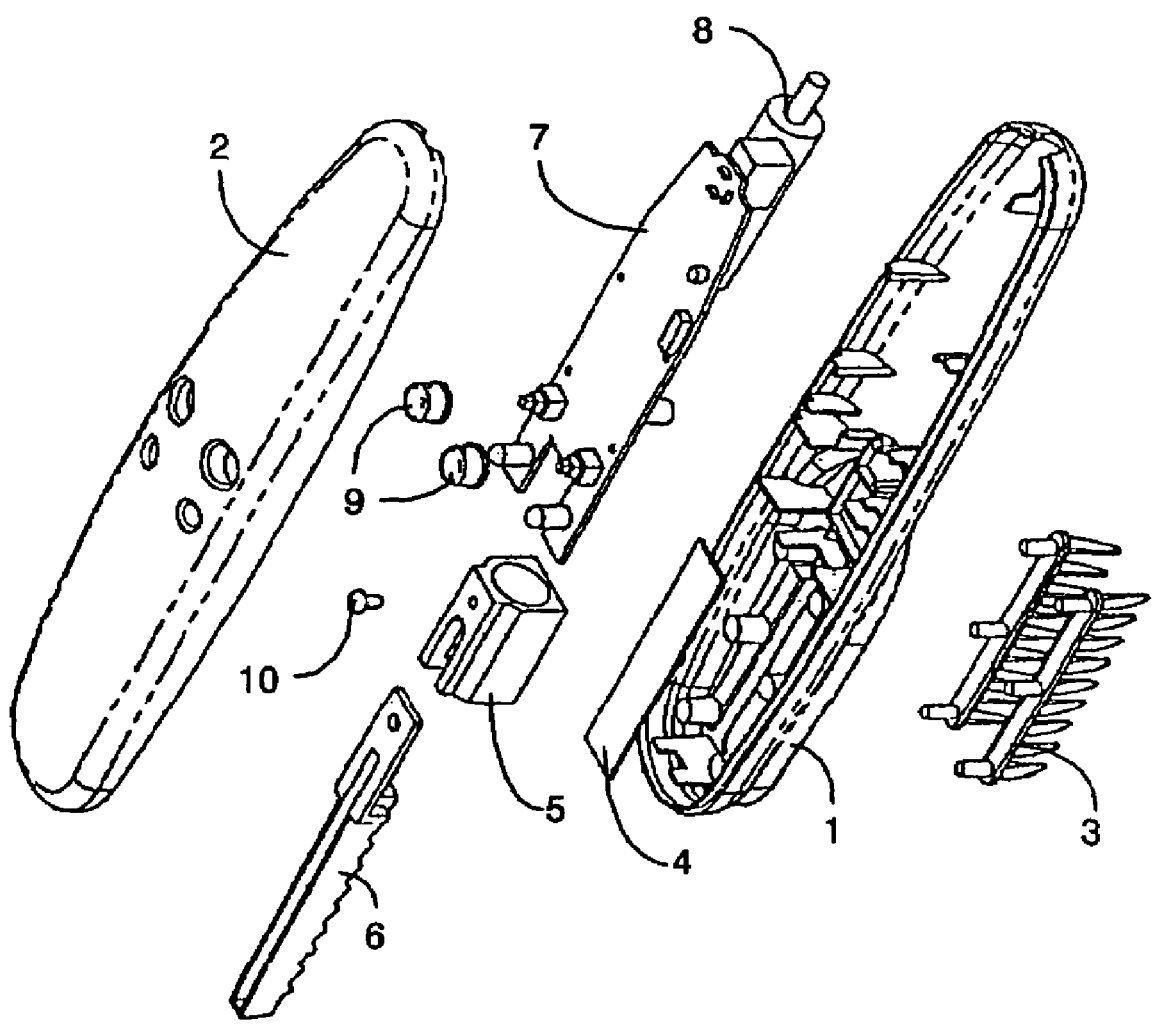
FIG. 5B is an exploded perspective view of a preferred embodiment of the device which illustrates its internal components.

FIG. 5B is an exploded view of the embodiment of FIG. 5A. In this embodiment, the various components of the system can be seen aligned with one another. The laser 8 is shown attached to a printed circuit board 7 which contains the control circuitry. The printed circuit board 7 is used to align the laser 8 with the coupling 5 that attaches to the reflector 6. By properly fabricating the various components of this device, individual alignment of each unit is unnecessary. As a result, manufacturing costs are substantially reduced. Also shown in this figure are lower housing 1, upper housing 2, teeth 3, switch caps 9, window 4, and associated hardware such as screw 10.

Figure 6:
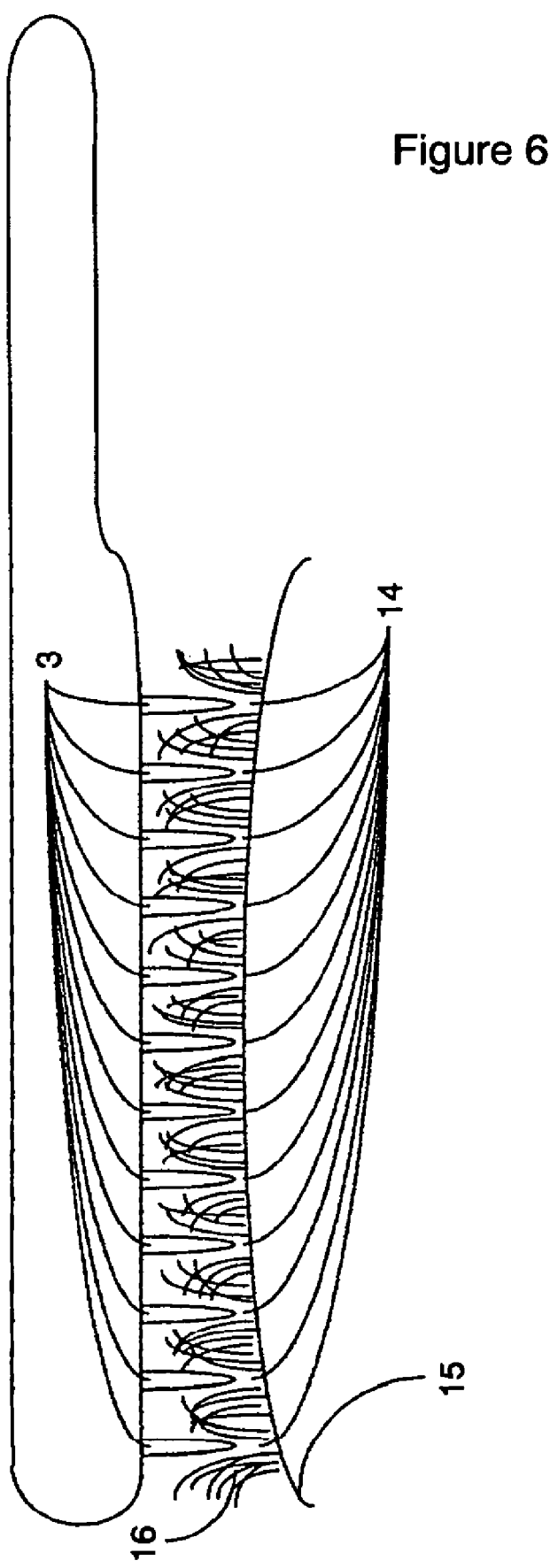
FIG. 6 is an illustration of a preferred embodiment of the device in which an individual's hair is being furrowed to maximize the amount of laser energy applied to the individual's scalp.

FIG. 6 illustrates how the teeth 3 were used to produce furrows 14 in the individual's hair 16. This figure has a side view illustrating the teeth 3 being pulled through the user's hair 16 while in close proximity to the user's scalp 15. As can be seen, the movement of the teeth 3 though the hair 16 pushes the hair 16 aside to form furrows 14. As the hair forms furrows 14, the scalp 15 between the teeth 3 is exposed. Since the laser beam is aligned between the two opposing teeth for each furrow 14, the laser beam is directed to the surface of the scalp 15 which has been exposed by the furrow 14. The advantage provided by furrowing the hair 16 is that a high percentage of the laser energy is effectively applied to the scalp 15, and the hair 16 is prevented from interfering with the application of laser energy to the scalp 15.

FIG. 7A illustrates an external side view of an alternative preferred embodiment in which the laser 8 is replaced with a non-coherent light source. In this embodiment, upper housing 2 and lower housing 1 support the set of teeth 3 in the same manner as was done in the foregoing embodiments. In addition, an activation switch 19 and a status indicator 20 are also shown.

FIG. 7B is a cutaway side view of the alternative preferred embodiment illustrated in FIG. 7A. In this figure, a power attachment plug 17 is illustrated. Plugs 17 attaches to a conventional power cord (not shown). Plugs 17 is attached to a power source 18 which is designed to distribute power to the various components under control off the power activation switch 19. When the device is activated, status indicator 20 is illuminated for the user's convenience.

Those skilled in the art will recognize that power supplies are well-known in the art, and that other changes can be made to power source 18. For example, power source 18 can be powered by batteries, by an input power source, via plugs 17, or by a combination of both.

Once the device has been activated, power will be supplied from the power source 18 to emitter control circuit 22. Emitters 21 are controlled by emitter control circuit 22 which regulates the amount of time that emitters 21 are active. As can be seen from this figure, emitters 21 are aligned with teeth 3. The light emitters 21 can be implemented by any suitable technology. However, in the preferred embodiment the emitters 21 are shown as LEDs for ease of discussion.

Figure 8A:
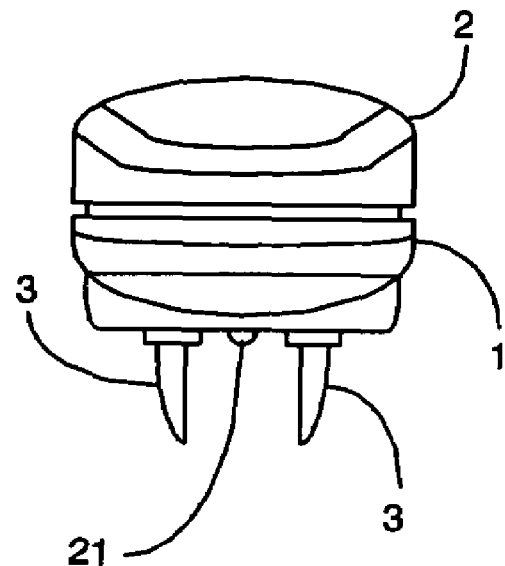
FIG. 8A is an external end view of the alternative preferred embodiment of FIG. 7A which illustrates the placement of the non-coherent light source between two rows of teeth.

In FIG. 8A, an external end view of the preferred embodiment of FIG. 7A is illustrated. Upper housing 2, lower housing 1 and teeth 3 are similar to those shown in the previous embodiments. In addition, the emitters 21 are also shown positioned between the teeth 3.

Figure 8B:
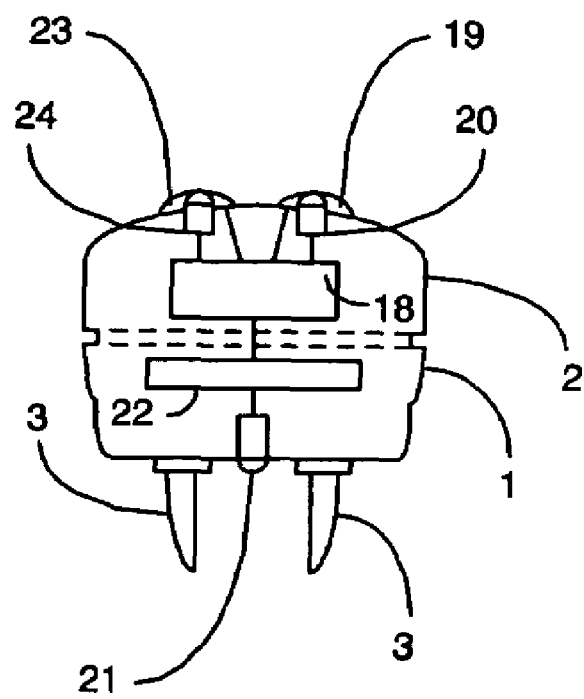
FIG. 8B is a cutaway end view of the alternative preferred embodiment of FIG. 7A.

FIG. 8B is a cutaway end view of the embodiment of FIG. 8A. When power activation switch 19 is activated, it activates power source 18. Once power source 18 is activated, it activates status indicator 20 which illuminates to indicate that power has been turned on. Also shown in this figure is emitter activation switch 23, which when turned on gates power to emitter control circuit 22 which then activates emitters 21.

FIG. 9A is a bottom external view of the embodiment of FIG. 7A. This view better illustrates how the emitters 21 are each aligned between associated pairs of teeth 3. Likewise, FIG. 9B illustrates a cutaway bottom view of the preferred embodiment of FIG. 7A. This view also illustrates the basic components of the system which are power source 18, the emitter control circuit 22, the emitters 21, the teeth 3, and the control switches 19, 23 and indicators 20, 24.

Figure 10A:
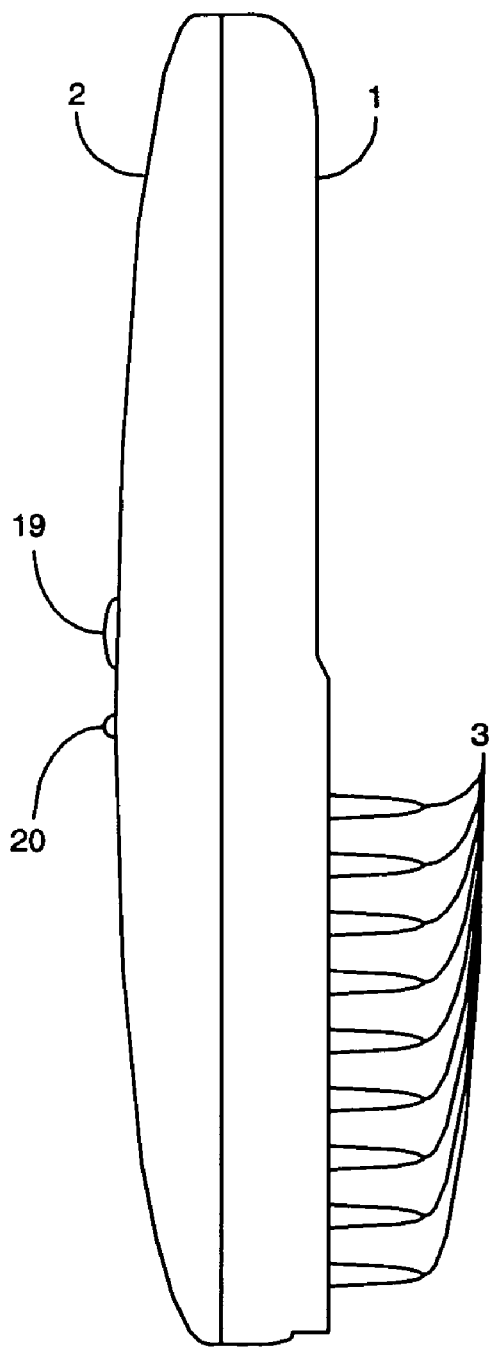
FIG. 10A is an external side view of another alternative preferred embodiment which provides both coherent and non-coherent light.

In FIG. 10A, a side external view of an alternative preferred embodiment is illustrated In this embodiment, the laser 8 which provided coherent light in previous embodiments is combined with emitters 21 which produce non-coherent light. As a result, energy can be concentrated in a small bandwidth by the laser 8, while broad bandwidth energy is simultaneously provided by the emitters 21.

Figure 10B:
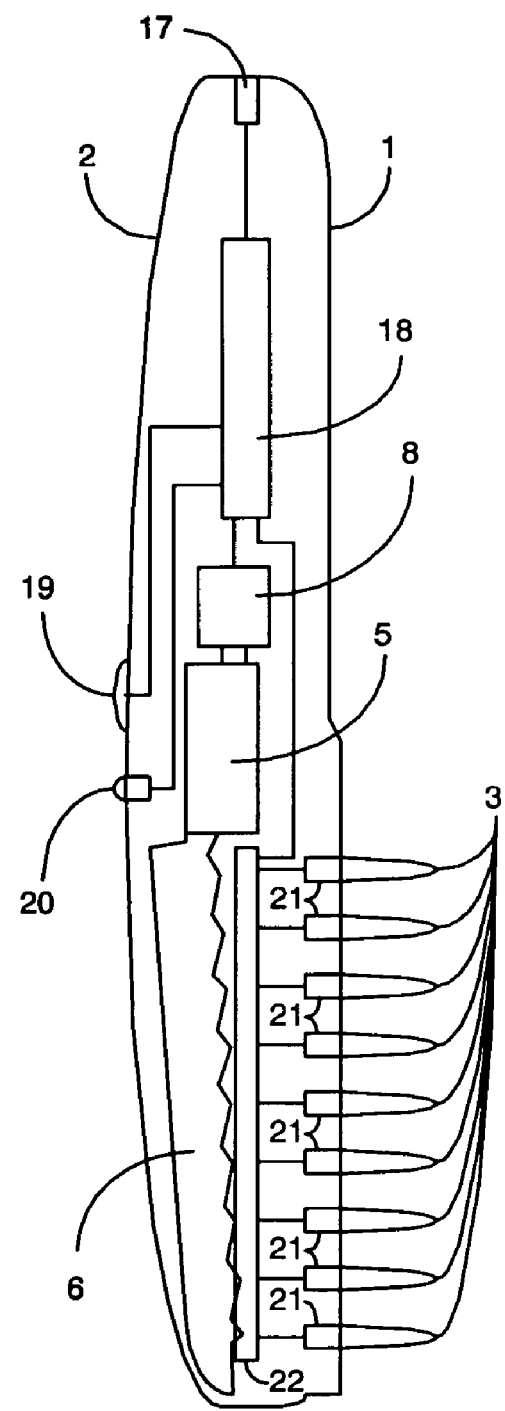
FIG. 10B is a cutaway side view of the preferred embodiment of FIG. 10A. This embodiment illustrates the main components of the coherent and non-coherent light emitting subsystems.

FIG. 10B is a side cutaway view of the preferred embodiment of FIG. 10A. This embodiment contains all the features of FIG. 7A, and in addition, it also contains the multiple beam laser components of the previous embodiments. When the power source 18 is activated, it provides power which can be gated to the laser 8 and to the emitter control circuit 22. As was the case above, the laser 8 generates a laser beam which passes through coupling 5 and is then split by reflector 6 into a plurality of parallel laser beams. Also shown in his figure are emitters 21 which are activated via emitter control circuit 22 and projects light towards the user's scalp.

Figure 11A:
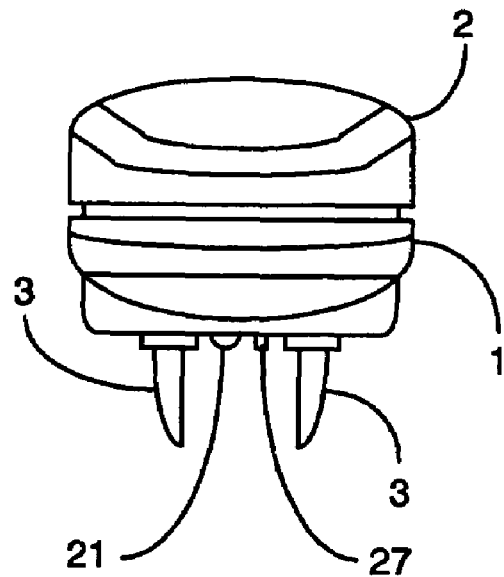
FIG. 11A is an external end view of the alternative preferred embodiment of FIG. 10A which illustrates the placement of the coherent and non-coherent light sources between two rows of teeth.

FIG. 11A is an external end view of the embodiment of FIG. 10A. This figure illustrates the upper housing 2, lower housing 1, and the teeth 3 shown in previous embodiments. In addition, it also illustrates the adjacent locations of the emitters 21 and the laser window 27.

Figure 11B:
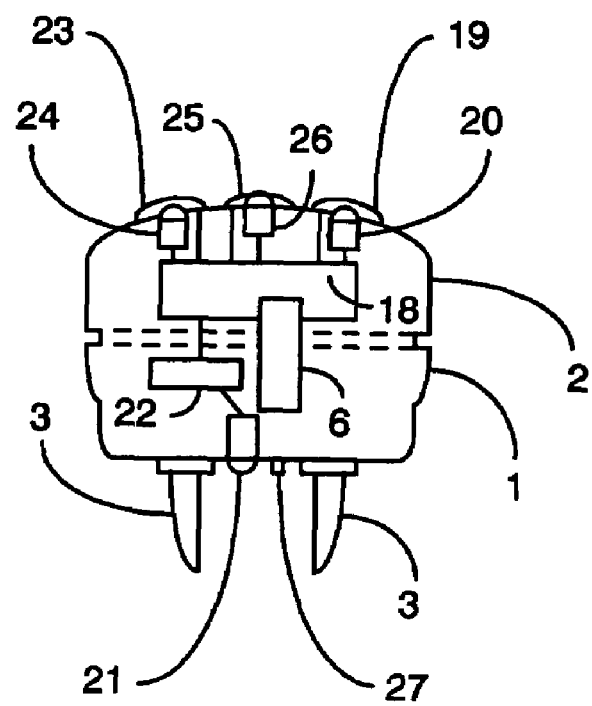
FIG. 11B is a cutaway end view of the alternative preferred embodiment of FIG. 10A.

FIG. 11B is an end cutaway view of the embodiment of FIG. 11A. This figure illustrates the side-by-side positioning of the emitters 21, and the laser reflector 5. In addition, this figure also illustrates a separate laser activation switch 25 and a laser status indicator 26.

In FIG. 12A, an external bottom view of the preferred embodiment of FIG. 10A is shown. This embodiment better illustrates the relative location of the emitters 21 in relation to the laser windows 27. Likewise, FIG. 12B is a bottom cutaway view of the embodiment of FIG. 12A. This figure also illustrates the side-by-side positioning of the components associated with the emitters 21, and the laser 8.

An advantage of this embodiment is that the patient can use the broadband power provided by the emitters 21 alone, the patient can use the narrow band concentrated laser power provided by the laser 8, or the patient can use both simultaneously.

While the invention has been described with respect to a preferred embodiment thereof, it will be understood by those skilled in the art that various changes in detail may be made therein without departing from the spirit, scope, and teaching of the invention. For example, the material used to construct the device may be anything suitable, the size and shape of the device can vary, the type of laser can vary, etc. Accordingly, the invention herein disclosed is to be limited only as specified in the following claims.

We claim:

1. A handheld hair treatment device, comprising:
   a non-coherent light source, outputting light that at least a portion of which has an approximate wavelength of a red-light source;
   a power supply for supplying power to the non-coherent light source;
   means to expose the scalp of an individual as the non-coherent light source is moved over the individual's scalp such that the light emanating from the non-coherent light source is substantially unobstructed from coming in contact with the scalp by the individual's hair;
   the means to expose the scalp further comprises a first plurality of hair deflecting means, each hair deflecting means associated with the non-coherent light source and positioned such that when the device is moved across an individual's scalp, each hair deflecting means creates an open light path in the hair in front of the light from the non-coherent light source and the light from the non-coherent light source is substantially unobstructed by the individual's hair;
   a second plurality of hair deflecting means, at least one hair deflecting means in the second plurality of hair deflecting means associated with at least one hair deflecting means in the first plurality of hair deflecting means such that they form a related pair of first and second hair deflecting means;
   at least one related pair of hair deflecting means are positioned such that the first hair deflecting means is positioned ahead of its associated second hair deflecting means such that when the device is moved across an individual's scalp, the first hair deflecting means creates an open light path to expose the scalp and the second hair deflecting means holds the open light path open while the non-coherent light source is moving across the individual's scalp;
   the non-coherent light source is comprised of a series of light emitting diodes;
   at least one light emitting diode is associated with an associated pair of first and second hair deflecting means, and further positioned between the first and second hair deflecting means such that when the device is combined through an individual's hair, an open light path is formed to provide an unobstructed path to the individual's scalp for light projected by the at least one light emitting diode;
   whereby the scalp of the individual is exposed during application of light to the scalp, and the amount of non-coherent light reaching the individual's scalp is maximized by the creation of open light paths in the individual's hair.

2. A handheld hair treatment device, comprising:
a non-coherent light source;
a power supply for supplying power to the non-coherent light source;
means to expose the scalp of an individual as the non-coherent light source is moved over the individual's scalp such that the light emanating from the non-coherent light source is substantially unobstructed from coming in contact with the scalp by the individual's hair;
and the means to expose the scalp further comprises a first plurality of hair deflecting means, each hair deflecting means associated with the non-coherent light source and positioned such that when the device is moved across an individual's scalp, each hair deflecting means creates an open light path in the hair in front of the light from the non-coherent light source and the light from the non-coherent light source is substantially unobstructed by the individual's hair;
the non-coherent light source is comprised of a series of light emitting diodes; and
each light emitting diode is associated with an associated pair of first and second hair deflecting means, and further positioned between the first and second hair deflecting means such that when the device is combed through an individual's hair, an open light path is formed to provide an unobstructed path to the individual's scalp for light projected by each light emitting diode;
whereby the scalp of the individual is exposed during application of light to the scalp, the amount of non-coherent light reaching the individual's scalp is maximized by the creation of open light paths in the individual's hair, and the device uses a plurality of light emitting diodes to project non-coherent light into the open light paths created by the hair deflecting means.

3. A device, as in claim 2, further comprising:
a second plurality of hair deflecting means, at least one hair deflecting means in the second plurality of hair deflecting means associated with at least one hair deflecting means in the first plurality of hair deflecting means such that they form a related pair of first and second hair deflecting means; and
at least one related pair of hair deflecting means are positioned such that the first hair deflecting means is positioned ahead of its associated second hair deflecting means such that when the device is moved across an individual's scalp, the first hair deflecting means creates an open light path to expose the scalp and the second hair deflecting means holds the open light path open while the non-coherent light source is moving across the individual's scalp;
whereby the related pairs of hair deflecting means hold the open light path open for an extended period of time while light is being directed to the individual scalp.

4. A device, as in claim 2, wherein the light output by the device has an approximate wavelength of a red-light source.

5. A device, as in claim 4, further comprising:
a red-light laser, outputting light that at least a portion of which has an approximate wavelength in the range of 632–670 nanometers.

6. A handheld hair treatment device, comprising:
a light source, further comprising:
a non-coherent light source;
a laser generator which produces a single laser beam; and a beam splitter is used to split the single laser beam into a plurality of separate laser beams, the laser beams oriented such that both laser beam energy produced by the laser generator and non-coherent light produced by the non-coherent light source are both directed toward the individual's scalp;
means to expose the scalp of an individual in the path of at least a portion of the light source as the light source is moved over the individual's scalp such that at least a portion of the light emanating from the light source is unobstructed from coming in contact with the individual's scalp; and
the light source suitable for application of light of the individual's scalp while the light source is in direct contact with the scalp and/or hair of the individual, or while the light source is not in direct contact with the scalp and/or hair of the individual;
a power supply for supplying power to the light source;
whereby the device emits both non-coherent light and laser energy, and at least a portion of the scalp of the individual is exposed during application of light to the scalp.

7. A device, as in claim 6, wherein the light output by the device has an approximate wavelength of a red-light source.

8. A device, as in claim 7, further wherein the approximate output wavelength of a red-light laser is in the range of 632–670 nanometers.

9. A device, comprising:
a non-coherent light source;
a power supply for supplying power to the non-coherent light source;
means to expose the scalp of an individual as the non-coherent light source is moved over the individual's scalp such that the light emanating from the non-coherent light source is substantially unobstructed from coming in contact with the scalp by the individual's hair;
a laser generator which produces a single laser beam;
a beam splitter is used to split the single laser beam into a plurality of separate laser beams, the laser beams oriented such that both laser beam energy produced by the laser generator and non-coherent light produced by the non-coherent light source are both directed toward the individual's scalp; and
the means to expose the scalp further comprises a first plurality of hair deflecting means, each hair deflecting means associated with the non-coherent light source and positioned such that when the device is moved across an individual's scalp, each hair deflecting means creates an open light path in the hair in front of the light from the non-coherent light source and the light from the non-coherent light source is substantially unobstructed by the individual's hair;
whereby the scalp of the individual is exposed during application of light to the scalp, and the amount of coherent and non-coherent light reaching the individual's scalp is maximized by the creation of open light in the individual's hair.

10. A device, as in claim 9, further comprising:
a second plurality of hair deflecting means, each hair deflecting means in the second plurality of hair deflecting means associated with a hair deflecting means in the first plurality of hair deflecting means such that they form a related pair of hair deflecting means ; and
each related pair of hair deflecting means are positioned such that the first hair deflecting means is positioned ahead of its associated second hair deflecting means such that when the device is moved across an individual's scalp, the first hair deflecting means creates a furrow to expose the scalp to the laser beam and the non-coherent light and the second holds the an open light path open while the device is moving across the individual's scalp;

whereby the related pairs of hair deflecting means hold the open light path open for an extended period of time while light is being directed to the individual's scalp.

11. A device, as in claim 10, wherein:

the non-coherent light source is comprised of a series of light emitting diodes; and each light emitting diode is associated with an associated pair of first and second hair deflecting means, and further positioned between the first and second hair deflecting means such that when the device is combed through an individual's hair, an open light path is formed to provide an unobstructed path to the individual's scalp for light projected by each light emitting diode;

whereby the device uses a plurality of light emitting diodes to project non-coherent light into the open light paths created by the hair deflecting means.

12. A device, as in claim 9, wherein the light output by the device has an approximate wavelength of a red-light source.

13. A device, as in claim 12, further wherein the approximate output wavelength of a red-light laser is in the range of 632–670 nanometers.

14. A method of beaming light energy toward an individual's scalp, including the steps of:

beaming non-coherent light energy toward the scalp of an individual by moving a handheld light generator across the individual's scalp, handheld light generator outputting light that at least a portion of which has an approximate wavelength of a red-light source;

maximizing the amount of light energy beamed toward the individual's scalp by deflecting hair away from the individual's scalp such that the light energy is not obstructed from coming in contact with the scalp by the individual's hair;

deflecting the hair away from the path of the light energy by creating an open light path in the individual's hair prior to beaming the light energy to the portion of the scalp in which the an open light path was created;

using a plurality of an open light path hair deflecting means to create an open light path s by parting the individual's hair prior to passing the light source over the individual's scalp;

extending the time in which the an open light path s remain open by using pairs of associated an open light path hair deflecting means to extend the time available for light energy to reach the user's scalp;

using a plurality of light emitting diodes as the non-coherent light source; and associating each light emitting diode with an associated pair of first and second hair deflecting means, and further positioning each light emitting diode between the first and second hair deflecting means such that when the device is combed through an individual's hair, a an open light path is formed to provide an unobstructed path to the individual's scalp for light projected beamed by each light emitting diode;

whereby individual's scalp is substantially unobstructed by hair during beaming of light energy to the scalp.

15. A method of applying light energy to an individual's scalp, including the steps of:

applying non-coherent light energy to the scalp of an individual by moving a handheld light generator across the individual's scalp;

maximizing the amount of light energy applied to the individual's scalp by deflecting hair away from the path of the light energy by creating a an open light path in the individual's hair prior to directing the light energy to the portion of the scalp in which the open light path was created such that the light energy is not obstructed from coming in contact with the scalp by the individual's hair;

deflecting hair away from ahead of light energy with a plurality of an open light path hair deflecting means to create an open light path s that part the individual's hair prior to passing the light energy over the individual's scalp;

using a plurality of light emitting diodes as the non-coherent light source; and associating each light emitting diode with an associated pair of first and second hair deflecting means, and further positioning each light emitting diode between the first and second hair deflecting means such that when the device is combed through an individual's hair, a an open light path is formed to provide an unobstructed path to the individual's scalp for light projected by each light emitting diode;

whereby the device uses a plurality of light emitting diodes to project non-coherent light into the an open light path s created by the hair deflecting means, and the individual's scalp is substantially unobstructed by hair during application of light energy to the scalp.

16. A method, as in claim 15, including the additional step of extending the time in which the an open light paths remain open by using pairs of associated hair deflecting means to extend the time available for light energy to reach the user's scalp.

17. A method, as in claim 15, wherein the light output by the device has an approximate wavelength of a red-light source.

18. A method, as in claim 17, including the additional steps of:

outputting light from a red-light laser that at least a portion of which has an approximate wavelength in the range of 632–670 nanometers.

19. A method of applying light energy to an individual's scalp, including the steps of:

applying non-coherent light energy to the scalp of an individual by moving a handheld light generator across the individual's scalp; and maximizing the amount of light energy applied to the individual's scalp by deflecting hair away from the path of the light energy by creating a an open light path in the individual's hair prior to directing the light energy to the portion of the scalp in which the open light path was created such that the light energy is not obstructed from coming in contact with the scalp by the individual's hair;

generating a single laser beam; and splitting the single laser beam into a plurality of separate laser beams, the laser beams oriented such that both laser beam energy and the non-coherent light are both directed toward the individual's scalp;

whereby the device emits both non-coherent light and laser energy, and the individual's scalp is substantially unobstructed by hair during application of light energy to the scalp.

20. A method, as in claim 17, including the additional step of:
splitting the laser beam with a multi-toothed beam refractor having a zigzag edge with a plurality of reflector hair deflecting means, and reflecting a portion of the laser beam with each reflector tooth;
whereby the portions of the laser beam created by the reflector hair deflecting means each form an independent laser beam.

21. A method, as in claim 20, including the additional step of:
arranging the laser beams and the non-coherent light source such that they are arranged in substantially parallel and adjacent areas in which both the laser energy and the non-coherent light arc both directed to the open light path.
whereby both the laser energy and the non-coherent light are applied to the surface of the individual's scalp which is exposed by the an open light paths.

22. A method, as in claim 21, including the additional step of:
providing independent means to activate or deactivate the laser and/or the non-coherent light source;
whereby the individual can selectively emit laser energy and/or non-coherent light.

23. A method, as in claim 19, wherein the light output by the device has an approximate wavelength of a red-light source.

24. A method, as in claim 23, including the additional step of:
outputting light from a red light laser having the approximate output wavelength in the range of 632–670 nanometers.

25. A handheld laser hair treatment device, comprising:
a housing and a handle;
a laser assembly secured within or to said housing for outputting a laser beam, said housing further including non-light emitting hair deflection means positioned such that the laser beam is between said hair deflection means, further comprising:
the laser beam having a light output at least a portion of which has an approximate wavelength of a red-light source, further, the laser beam being emitted at a distance from the individual's scalp and projected from the laser assembly toward the individual's scalp; and
a power source for supplying power to the laser beam assembly;
whereby the scalp of the individual is exposed during application of energy from the laser beam to the scalp.

26. A device, as in claim 25, wherein:
the laser beam assembly produces a plurality of laser beams, each laser beam spaced apart from one another;
the means to expose the scalp further comprises a first plurality of hair deflecting means, each hair deflecting means associated with a laser beam and positioned such that when the device is moved across an individual's scalp, each hair deflecting means creates an open light path in the hair in front of the laser beam and the laser beam is substantially unobstructed by the individual's hair;
whereby the amount of laser energy reaching the individual's scalp is maximized by the creation of open light paths in the individual's hair.

27. A method of applying laser energy to an individual's scalp, including the steps of:
applying laser energy, at least a portion of the laser energy having an approximate wavelength of a red-light source, to the scalp of an individual by moving a handheld laser generator across the individual's scalp, the laser generator separated from the individual's scalp and projecting a laser beam from the laser generator toward the individual's scalp;
deflecting the hair away from the path of the laser beam by parting the hair to create an open light path in the individual's hair in advance of the passing laser beam with non-laser carrying hair deflecting means to maximize the amount of laser
energy applied to the scalp of the individual by deflecting hair away from the of an individual scalp such that the laser beam is not obstructed from coming in contact with the scalp by the individual's hair;
whereby the laser beam has an unobstructed path from the laser generator to the scalp of the individual.

28. A method, as in claim 27, including the additional step of extending the time in which the open light paths remain open by using pairs of hair deflecting means, associated with a laser beam, and positioned in front of and to the rear of the laser beam.

* * * * *